US00PP25910P3

(12) United States Plant Patent
Olesen

(10) Patent No.: US PP25,910 P3
(45) Date of Patent: Sep. 22, 2015

(54) HYBRID TEA ROSE PLANT NAMED 'POULHT008'

(50) Latin Name: ***Rosa* hybrid**
Varietal Denomination: Poulht008

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 168 days.

(21) Appl. No.: 13/986,913

(22) Filed: Jun. 14, 2013

(65) Prior Publication Data

US 2014/0373222 P1 Dec. 18, 2014

(51) Int. Cl.
*A01H 5/02* (2006.01)

(52) U.S. Cl.
USPC ..... Plt./137

(58) Field of Classification Search
USPC ..... Plt./101, 130, 137
See application file for complete search history.

(56) References Cited

PUBLICATIONS

UPOV-PLUTO Plant Variety Database, International Union for Protection of New Varieties of Plants, Jan. 19, 2015, obtained for cultiver 'Poulht008' (1 page total).*
'HelpMeFind' website for roses, clematis and peonies. Cultivar 'Poulht008'. Retrieved from the Internet http://www.helpmefind.com/rose/pl.php?n=88787 (1 page total).*
"Poulsen Roser A/S" catalog; Retrieved from the Internet http://www.poulsenroser.com (2 pages total).*
"Catalogorosales" Retrieved from the Internet http://www.viverosguzman.es/contenido/descargas/rosales.pdf (9 pages total).*

* cited by examiner

*Primary Examiner* — Susan McCormick Ewoldt

(57) ABSTRACT

A new garden rose plant of the Hybrid Tea class which has abundant, pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulht008'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2005 and the resulting seeds were planted in a controlled environment in Fredensborg, Denmark. The new variety, named 'Poulht008', originated as a single seedling from the stated cross.

The new variety may be distinguished from its male pollen parent and female seed parent primarily by flower coloration. The female seed parent has light pink flowers, while the claimed plant has pink flowers. The male pollen parent has light red flowers.

The objective of the hybridization of this rose variety was to create a new and distinct variety for garden use with unique qualities, such as:

1. Abundant and uniform pink, fragrant, flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulht008' from all other varieties of which we are aware.

As part of the rose development program, Mogens N. Olesen germinated the seeds from the aforementioned hybridization during winter of 2005 and conducted evaluations on the resulting seedlings in a controlled environment in Fredensborg, Denmark. 'Poulht008' was selected in the spring of 2006 by the inventor as a single plant from the progeny of the aforementioned hybridization.

Asexual reproduction of 'Poulht008' by traditional budding and rooted cuttings was first done by Mogens N. Olesen in the nursery in Fredensborg, Denmark in July, 2006. This initial and other subsequent asexual propagations conducted in controlled environments have demonstrated that the characteristics of 'Poulht008' are true to type and are transmitted from one generation to the next.

DESCRIPTION OF THE DRAWINGS

The accompanying color illustration shows as true as is reasonably possible to obtain in color photographs of this type, the typical characteristics of the buds, flowers, leaves, and stems, of 'Poulht008'.

Specifically illustrated in the drawing are flowers at various stages of development, flower in parts, leaves, and stems. Illustrated plants are 2 years of age.

DETAILED DESCRIPTION OF THE VARIETY

Figure 1:
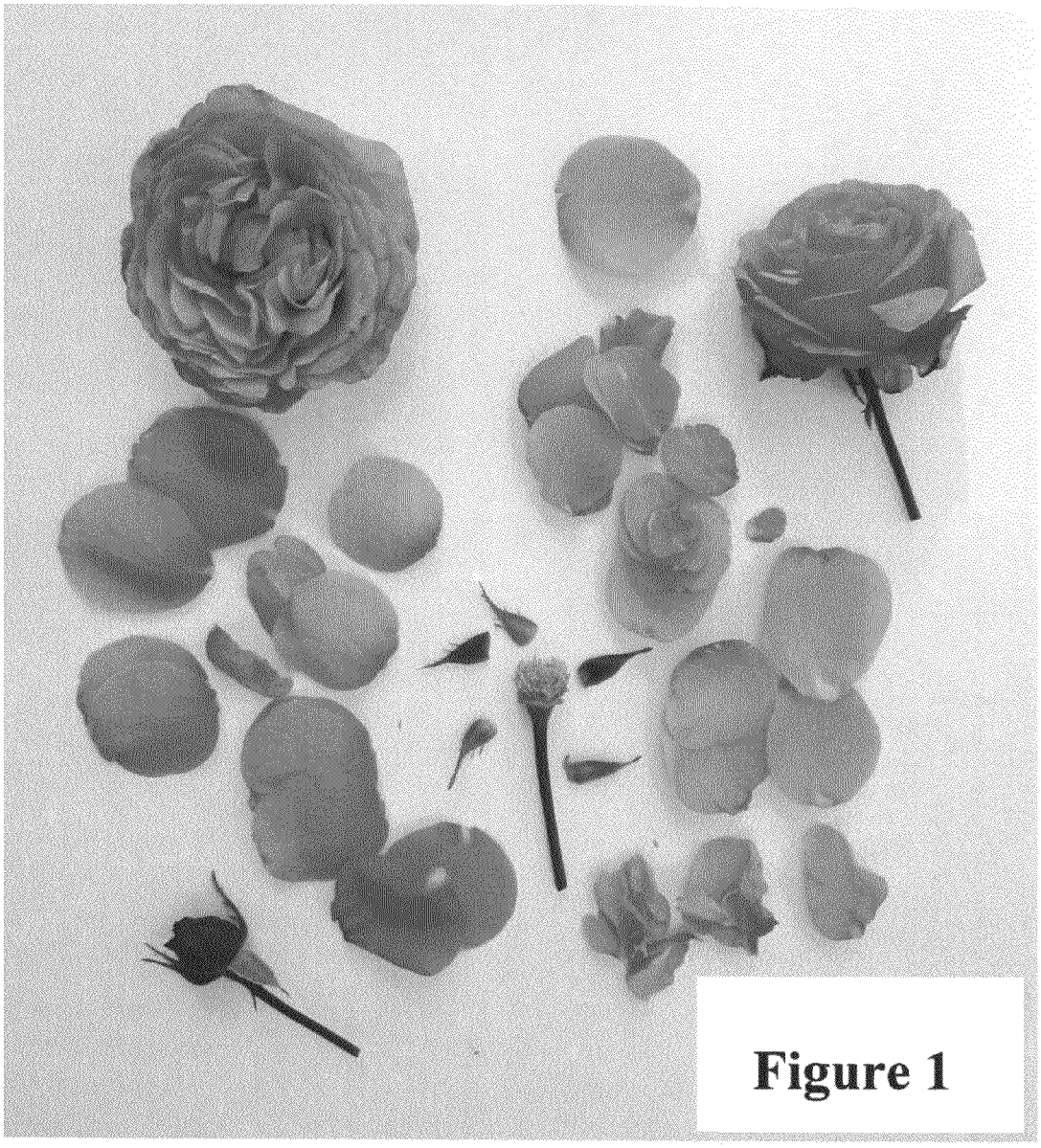
Figure 2:
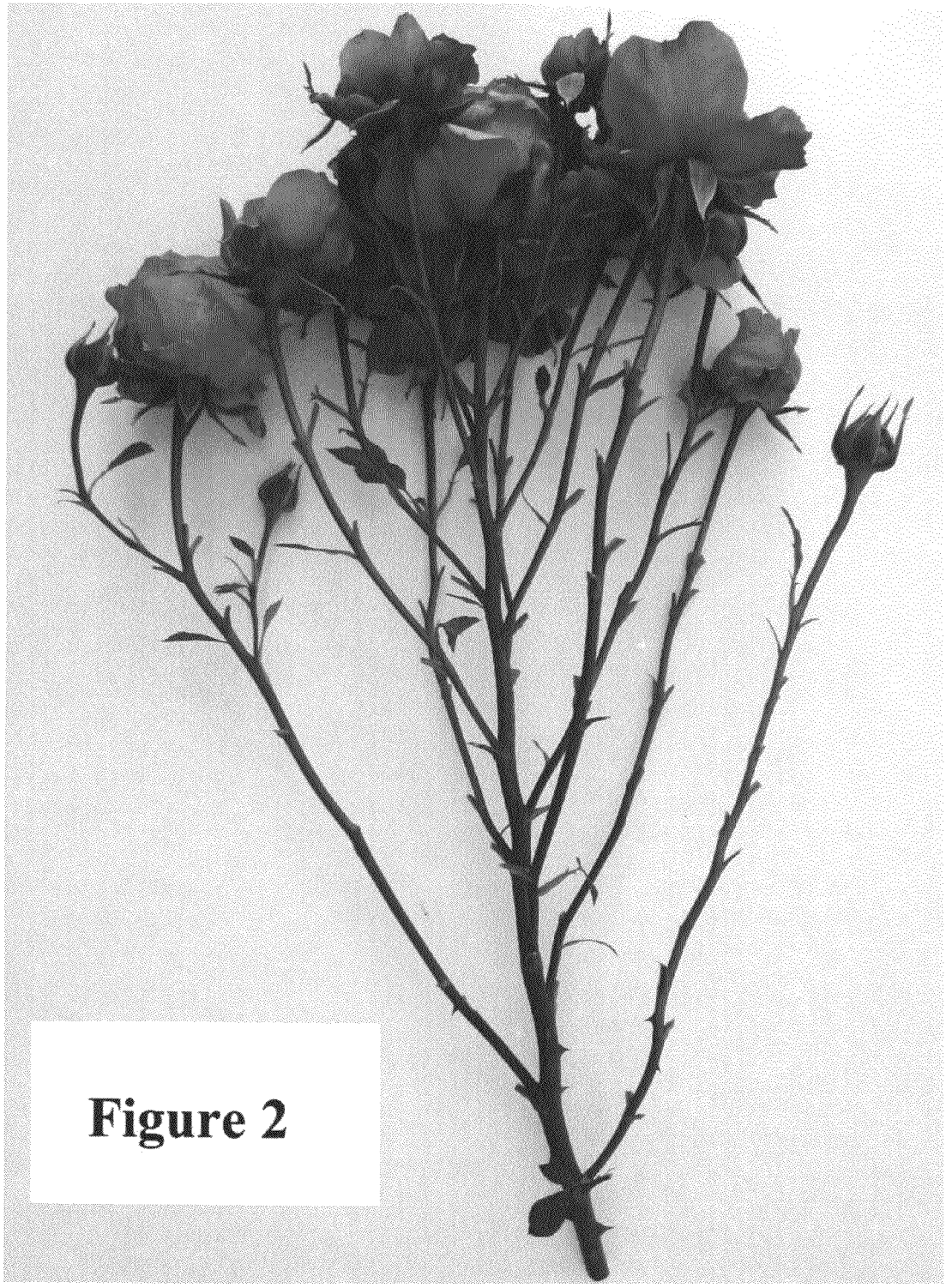
Figure 3:
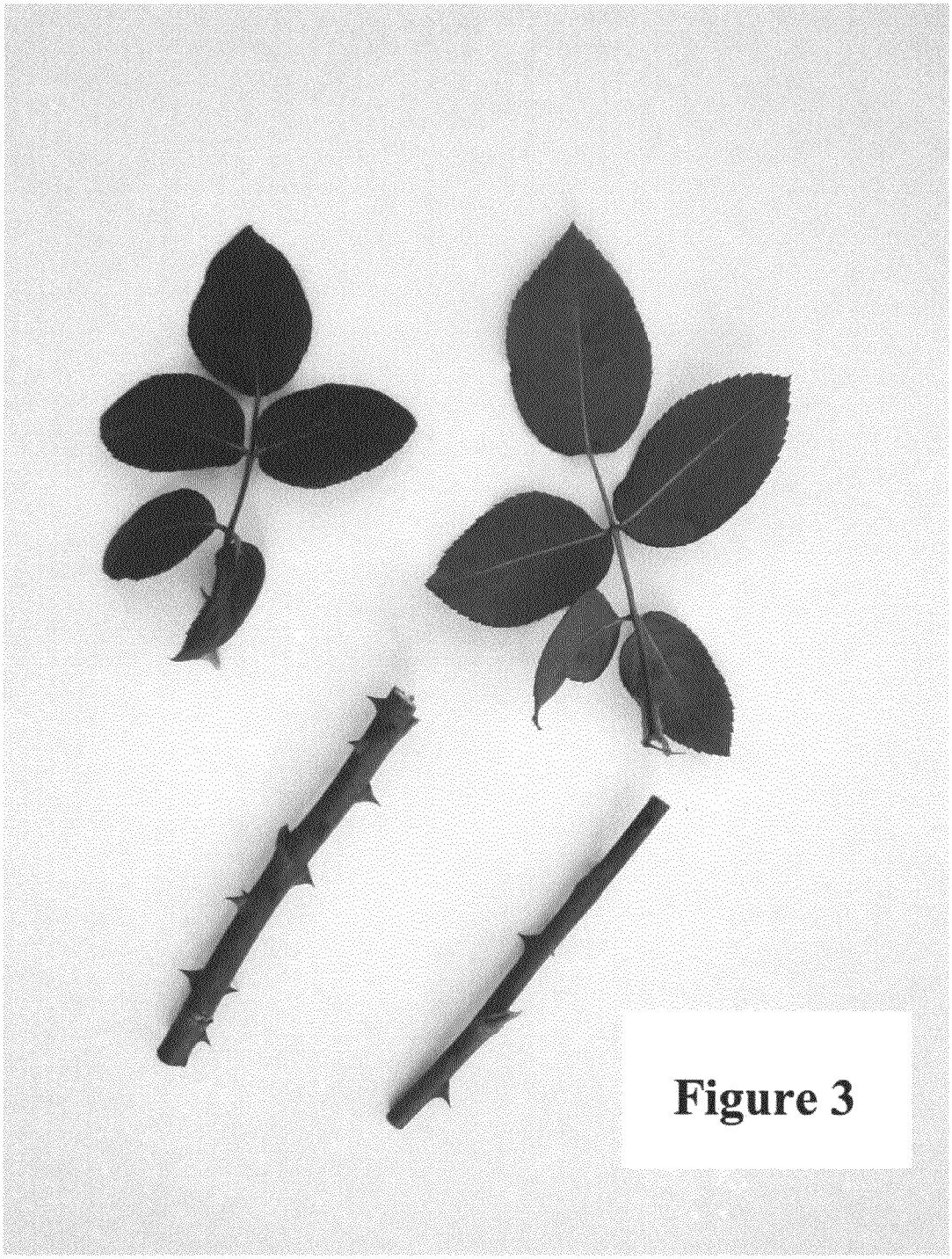

The following is a description of 'Poulht008', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulpm002', U.S. Plant Pat. No. 15,383 are compared to 'Poulht008' in Chart 1.

CHART 1

| | 'Poulht008' | 'Poulpm002' |
|---|---|---|
| Petal Count | 85 petals total, 15 to 20 of which are petaloids | 26 to 30 petals under normal conditions with 6 petaloids |
| Flower Diameter | 85 mm | 65 mm |
| General Tonality of Flower Color | Red Group 52B and Red 52C | Red Group 55B to Red-Purple Group 63C |

Flower and Flower Bud

Blooming habit: Continuous.

Flower bud:

*Size.*—Upon opening, 25 mm in length from base of receptacle to end of bud. Bud diameter is 20 mm.

*Bud form.*—Urceolate.

*Bud color.*—As sepals divide Red Group 45A.

*Sepal inner surface.*—Color: Green Group 138 A. Surface: Smooth.

*Sepal outer surface.*—Color: Yellow-Green Group 144A with strong anthocyanin, the color of Greyed-Orange Group 176A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—40 mm long by 10 mm wide.

*Receptacle.*—Texture: Smooth. Size: 10 mm in height by 8 mm wide. Color: Yellow-Green Group 144A. Anthocyanic pigments the color of Greyed-Red Group 178A observed. Shape: Funnel.

*Pedicel.*—Surface: Smooth. Length: 20 to 45 mm. Diameter: 3 to 4 mm. Color: Yellow-Green Group 144C with Red Group 178A. Strength: Moderate.

*Peduncle.*—Length: 20 to 5 cm. Diameter: 5 mm. Texture: Smooth. Color: Yellow-Green Group 144A with strong intonations of Greyed-Red Group 178A.

Flower bud development: Flower buds are borne in clusters of approximately 15 flower buds per stem, resembling a corymb.

Flower bloom:

*Fragrance.*—Strong perfume.

*Duration.*—The blooms have a duration on the plant of approximately 10 days. Petals fall cleanly away from plant after flowers have fully matured.

*Size.*—Flower diameter is 85 mm when open. Flower depth is 45 mm.

*Flower shape.*—General shape is typical for a hybrid tea, with a high pointed center which is tightly closed.

*Shape of flower, side view.*—The upper portion is flat. Lower portion is concave.

Petalage: Under normal conditions, flowers have 85 petals total, 15 to 20 of which are petaloids.

General tonality of flower: Open flowers are Red Group 52B and Red 52C. Tonality changes to Red Group 52D as the flower ages.

Petal color:

*Upon opening, outer petals.*—Upper surface: Red Group 52C. Lower surface: At basal zone Red-Purple Group 58B. Middle and marginal zones are Red-Purple Group 61D.

*Upon opening, inner petals.*—Upper surface: Combination of Red Group 52C and Red Group 43C. Lower surface: At basal zone Red-Purple Group 58B. Middle and marginal zones are Red-Purple Group 61D.

*Basal petal spots.*—Yellow Group 2B on lower and upper surface.

*After opening, outer petals.*—Upper surface: Red Group 54C. Lower surface: At basal zone Red-Purple Group 58B. Middle and marginal zones are Red-Purple Group 61D.

*After opening, inner petals.*—Upper surface: Red Group 54C with intonations of Red Group 52C. Lower surface: At basal zone Red-Purple Group 58B. Middle and marginal zones are Red-Purple Group 61D. Basal petal spots: Yellow Group 2B on lower and upper surface.

Petals:

*Petal reflex.*—Absent.

*Margin.*—Entire and uniform. No undulations of margin observed.

*Shape.*—Broadly to narrow elliptic. Apex shape: Rounded. Base shape: Acute.

*Size.*—60 mm (l) 50 mm (w).

*Texture.*—Smooth.

*Thickness.*—Average.

Petaloids:

*Size.*—25 mm (l) by 15 mm (w).

*Quantity.*—15 to 20.

*Shape.*—Apex is rounded, base is acute.

*Margins.*—Strong undulations.

*Color.*—Red-Purple Group 58A on lower surface. Upper surface is Red Group 43C.

Reproductive organs:

*Pollen.*—None observed.

*Anthers.*—Size: 3 mm in length. Color: Yellow Group 8B. Quantity: 70 on average.

*Filaments.*—Color: Yellow Group 9C. Length: 8 mm.

*Pistils.*—Length: 10 mm. Quantity: 60 on average.

*Stigmas.*—Color: Greyed-Yellow Group 162C.

*Styles.*—Color: Red Group 45C.

*Location of stigmas.*—Superior in location relative to the length of the filaments and the height of the anthers.

*Hips.*—None Observed.

Plant

Plant growth: Upright. Plants are 80 cm in height, and 65 cm wide.

Stems:

*Color.*—Juvenile growth: Yellow-Green Group 144A with strong intonations of Greyed-Red Group 178A. Mature growth: Yellow-Green Group 144A.

*Length.*—On average, canes are 40 cm from the base of the plant to the flowering portion.

*Diameter.*—11 mm.

*Internodes.*—On mature canes, there is an average distance of 45 mm between nodes.

*Surface texture.*—Young wood: Smooth. Older wood: Smooth.

Long prickles:

*Incidence.*—8 prickles per 10 cm of stem.

*Size.*—Average length of prickles on mature stems is 9 mm.

*Shape.*—Upper portion and lower portion are concave.

*Color.*—Juvenile prickles: Greyed-Purple Group 187C. Mature prickles: Greyed-Purple Group 183B.

Plant foliage:

*Compound leaf.*—150 mm (l)×100 (w).

*Quantity.*—2 leaves per 10 cm of stem on average.

*Leaf bearing angle to the stem.*—60 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 25 mm in length. Quantity: 2 per compound leaf. Shape: Linear, slightly broad based with outward extending apecies. Margins: Finely serrated with few stipitate glands. Color: Yellow-Green Group 144A.

*Petiole.*—Length: 35 mm. Diameter: 2 mm. Upper surface: Color: Yellow-Green Group 144C. Lower surface: Color: Yellow-Green Group 144B.

*Rachis.*—Length: 50 mm. Upper surface: Color: Yellow-Green Group 144C. Lower surface: Color: Yellow-Green Group 144B.

*Leaflet.*—Quantity: Normal number of leaflets leaves in middle of the stem is 5 leaflets. Margins: Serrulate. Size: Average size of the terminal leaflet on normal leaves is 60 mm in length by 40 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Hybrid Tea rose class named 'Poulht008', substantially as illustrated and described herein, due to its abundant pink flowers, disease resistance, and extended period of bloom.

* * * * *